(12) United States Patent
El Bakkouri et al.

(10) Patent No.: US 7,754,707 B2
(45) Date of Patent: Jul. 13, 2010

(54) METHODS OF TREATMENT OF CHRONIC IMMUNE DISEASE

(75) Inventors: Karim El Bakkouri, Anderlecht (BE); Patrick Englebienne, Zingem (BE); Kenny De Meirleir, Mechelen (BE); Charles Vincent Herst, Oakland, CA (US)

(73) Assignee: R.E.D. Laboratories, N.V./S.A., Zellik (BE)

( * ) Notice: Subject to any disclaimer, the term of this patent is extended or adjusted under 35 U.S.C. 154(b) by 1618 days.

(21) Appl. No.: 10/882,993

(22) Filed: Jun. 30, 2004

(65) Prior Publication Data

US 2005/0032770 A1   Feb. 10, 2005

Related U.S. Application Data

(63) Continuation of application No. PCT/US03/07001, filed on Jan. 10, 2003.

(60) Provisional application No. 60/349,915, filed on Jan. 17, 2002.

(51) Int. Cl.
 *A61K 31/545* (2006.01)
(52) U.S. Cl. .................. 514/206; 514/200; 514/202; 514/203; 514/204
(58) Field of Classification Search .................. 514/200, 514/206, 202–204
 See application file for complete search history.

(56) References Cited

U.S. PATENT DOCUMENTS

| | | | |
|---|---|---|---|
| 5,409,917 A | 4/1995 | Robinson et al. | |
| 5,766,859 A | 6/1998 | Vojdani et al. | |
| 5,776,690 A | 7/1998 | Vojdani et al. | |
| 5,830,668 A | 11/1998 | Mordechai et al. | |
| 5,853,996 A | 12/1998 | Mordechai et al. | |
| 5,877,197 A * | 3/1999 | Karanewsky et al. | 514/397 |
| 5,985,565 A | 11/1999 | Suhadolnik | |
| 6,080,554 A * | 6/2000 | Campine et al. | 435/21 |
| 2003/0114449 A1* | 6/2003 | Aranyi et al. | 514/233.2 |

FOREIGN PATENT DOCUMENTS

| | | |
|---|---|---|
| WO | WO 91/00097 | 1/1991 |
| WO | WO 9815646 A1 * | 4/1998 |
| WO | WO 0051623 A2 * | 9/2000 |
| WO | WO 00/65086 | 11/2000 |
| WO | WO 0112184 A1 * | 2/2001 |

OTHER PUBLICATIONS

Dllegri et al. Cefoperazone prevents the inactivation alpha 1 antitrypsin by activated neurophils, Antimicrobial agents and chemotherapy, 1999, vol. 43, No. 9, p. 2307-2310.*
Castelli et al. "A Study of the Interferon Antiviral Mechanism: Apoptosis Activation by the 2-5A System," *The Journal of Experimental Medicine* (1997) 186(6):967-972.
Diaz-Guerra et al. "Activation of the IFN-Inducible Enzyme RNase L Causes Apoptosis of Animal Cells," *Virology* (1997) 236:354:363.

* cited by examiner

*Primary Examiner*—Shengjun Wang
(74) *Attorney, Agent, or Firm*—Bret E. Field; Bozicevic, Field & Francis LLP

(57) ABSTRACT

Methods for treating a host suffering from a chronic immune disease, e.g., MS or CFS, are provided. In practicing the subject methods, an effective amount of an elastase inhibitory agent, e.g., a β-lactam containing compound, is administered to the host. Also provided are compositions for use in practicing the subject methods.

9 Claims, 4 Drawing Sheets

The *In Vitro* Effects of Elastase on Recombinant RNase L Protein

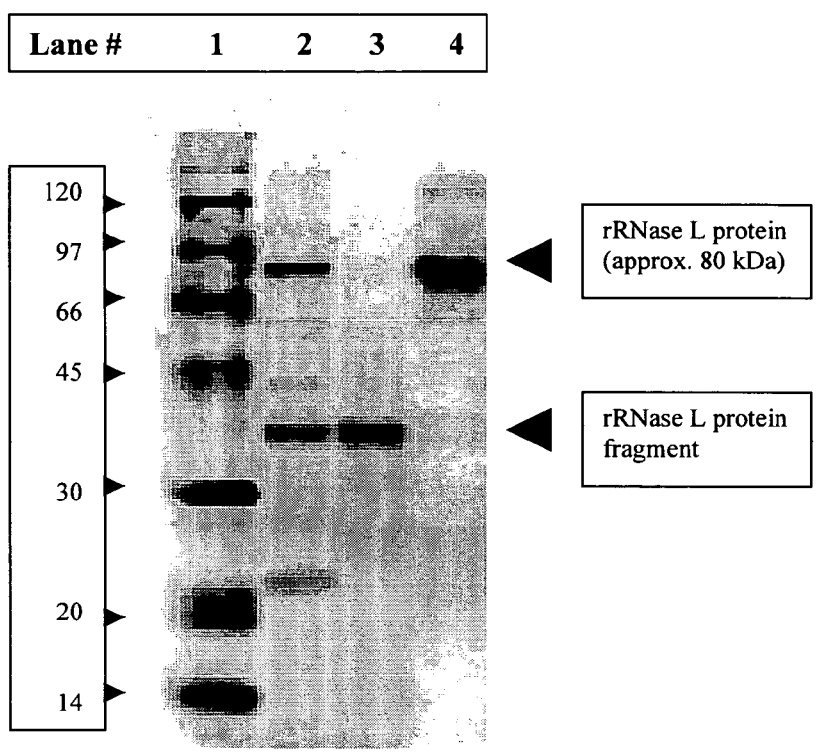
Figure 1 –   The *In Vitro* Effects of Elastase on Recombinant RNase L Protein

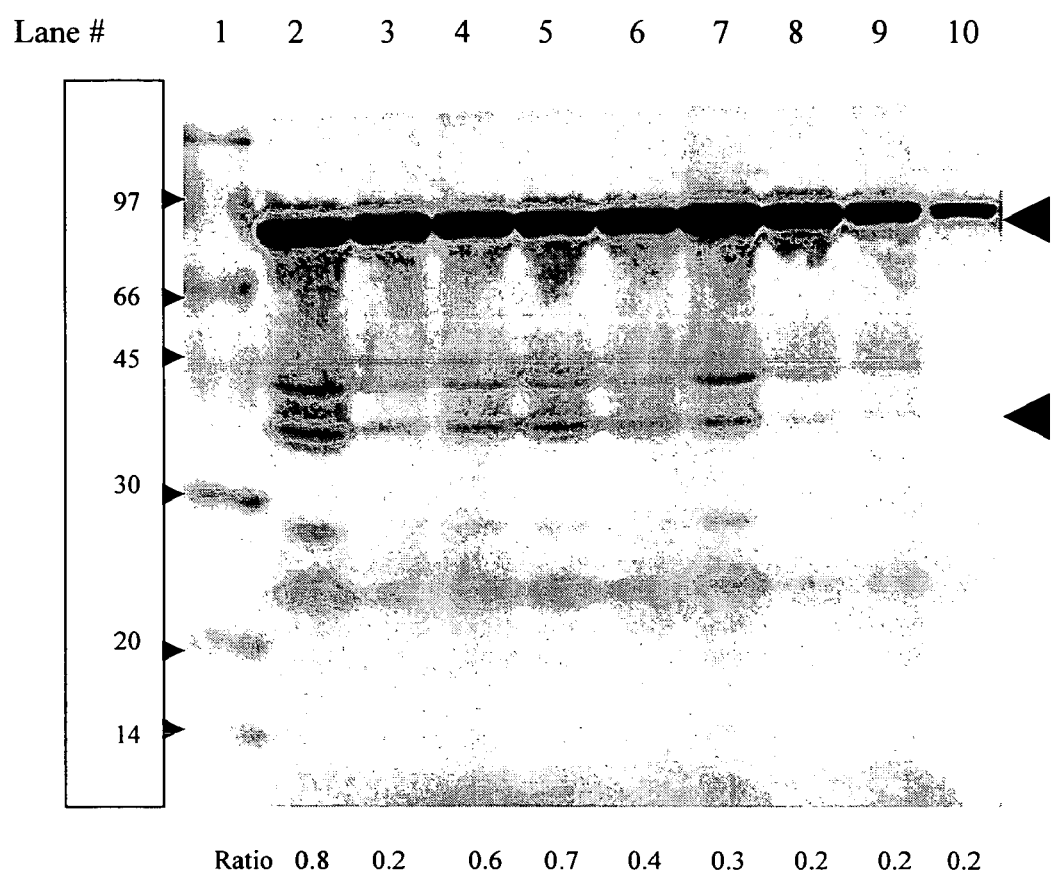
Figure 2  The *In Vitro* Effects of Cefoperazone on the Levels of RNase L Protein Fragmentation in U937 Cells

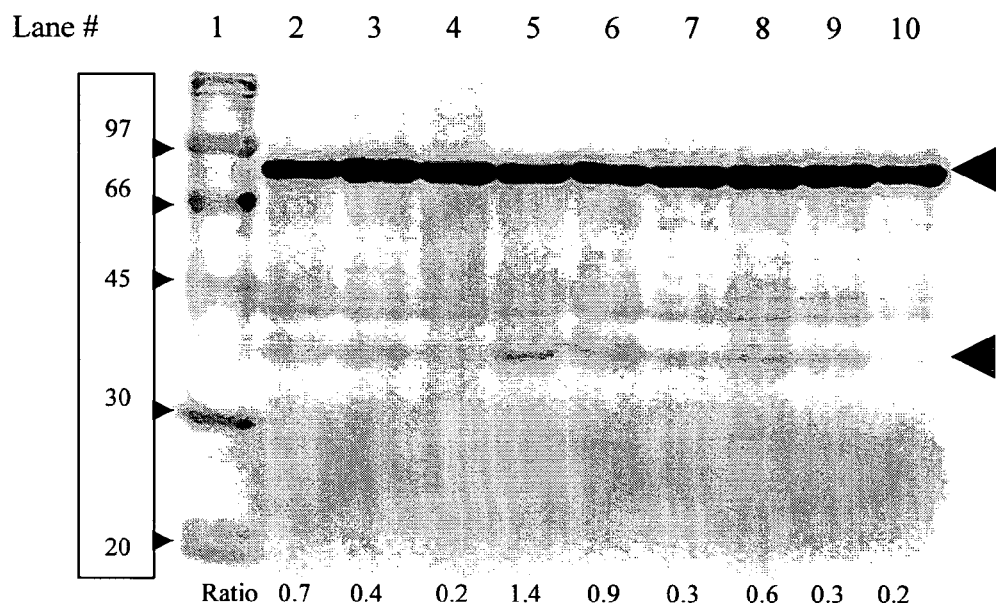
Figure 3    The *In Vitro* Effects of Cefoperazone on the Levels of RNase L Protein Fragmentation in U937 Cells

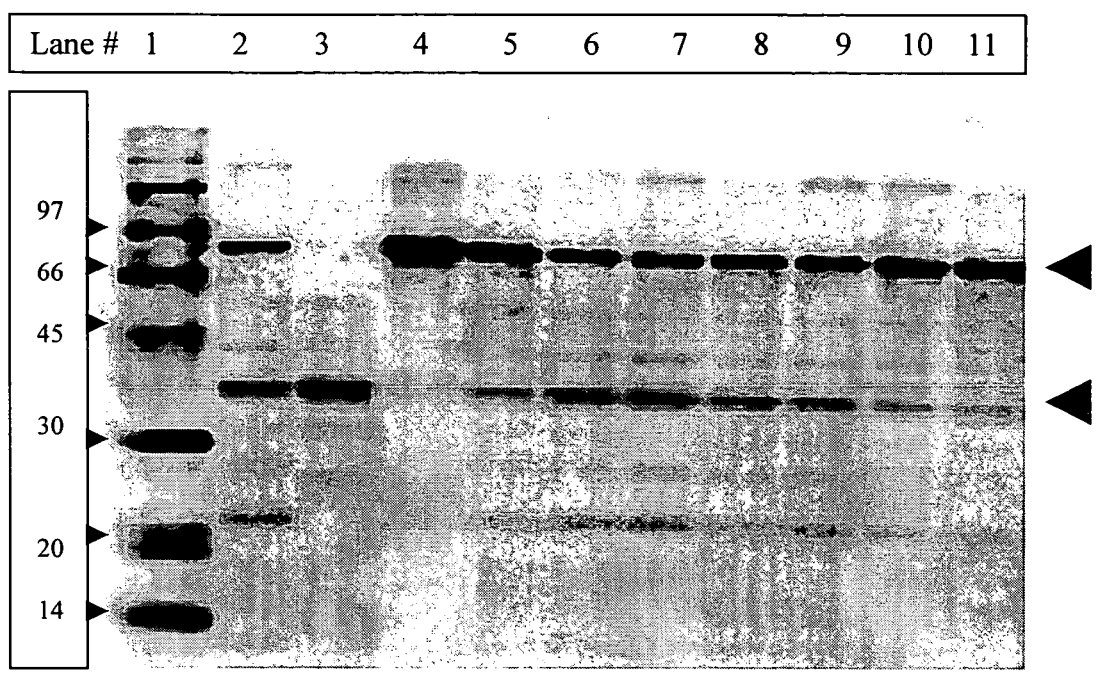
Figure 4    The *In Vitro* Effects of Cytoplasmic Protein Extracts from U937 Cells Previously Treated with Cefoperazone on Recombinant RNase L Protein

METHODS OF TREATMENT OF CHRONIC IMMUNE DISEASE

CROSS-REFERENCE TO RELATED APPLICATIONS

This application is a continuation of application serial no. PCT/US03/00701 filed on Jan. 10, 2003; which application, pursuant to 35 U.S.C. § 119 (e), claims priority to the filing date of the U.S. Provisional Patent Application Ser. No. 60/349,915 filed Jan. 17, 2002; the disclosures of which are herein incorporated by reference.

INTRODUCTION

1. Technical Field

The field of this invention is chronic immune disease, particularly chronic fatigue syndrome and multiple sclerosis.

2. Background of the Invention

Chronic immune diseases can be highly debilitating. Two such chronic immune diseases are multiple sclerosis and chronic fatigue syndrome.

Multiple sclerosis (MS) is a neurological illness of unknown etiology associated with attacks of focal or multifocal neurological dysfunction arising from lesions within the central nervous system (CNS). In America and Northern Europe, MS is the most common neurological disease, with prevalence rates estimated between 50-100 per 100,000 in the population. The onset of disease is most common in early adulthood. Recurrent attacks can occur over many years, with approximately 30 percent of the patients progressing to a severe form of the disease that can be fatal.

MS is pleomorphic in its presentation. The clinical manifestations are determined in part by the location of the foci of demyelination within the CNS. Classical features of the disease include impaired vision, nystagmus, dysarthria, ataxia and intention tremor, and weakness/paralysis of one or more limbs.

The most common form of the disease is episodic. Symptoms develop with subsequent recovery, then another attack occurs. In approximately 50 percent of all patients with MS, attacks become more frequent, usually with a worsening of symptomatology. In 30 percent of all patients, the disease develops into what is referred to as progressive/relapsing, the most severe form of the disease. In this state remissions are rare and patients frequently become wheelchair bound.

A number of new therapies for MS have been approved for use in the last few years, all based on the administration of Interferon (IFN), primarily IFN-beta, in various forms and dosages. However, in many instances this drug is poorly tolerated and often is associated with side effects that cause the patient to discontinue taking the medication. One recent study indicated that only 8-10 percent of MS patients would benefit from IFN-beta therapy. It is currently unknown as to why IFN only works in a subset of patients. More effective and less toxic therapies are needed, as is an understanding of when the administration IFN may be most useful in the course of the disease.

Like MS, chronic fatigue syndrome (CFS) is an illness of unknown etiology. CFS is often associated with sudden onset, flu-like symptoms, debilitating fatigue, low-grade fever, myalgia and neurocognitive dysfunction. CFS patients typically display reduced Karnofsky performance scores (KPS). The Karnofsky performance test measures an individual's ability to function and carry on normal activities. Karnofsky scores range form zero for a nonfunctional or dead patient to 100 for a completely normal function.

There continues to be a need for the identification of new treatment therapies for chronic immune disease.

RELEVANT LITERATURE

U.S. patents of interest include: U.S. Pat. Nos. 5,409,917; 5,766,859; 5,776,690; 5,830,668; 5,853,996; and 5,985,565. Also of interest is WO 91/00097 and WO 00/65086. Other references of interest include: Castelli et al. (1997), *J. Exp. Med.* 186:967-972 and Diaz-Guerra et al. (1997), *Virology* 236:354-363.

SUMMARY OF THE INVENTION

Methods for treating a host suffering from a chronic immune disease, e.g., MS or CFS, are provided. In practicing the subject methods, an effective amount of a protease-inhibitory agent, and in many embodiments an elastase-inhibitory agent, e.g., a β-lactam containing agent, is administered to the host. Also provided are compositions and kits thereof for use in practicing the subject methods.

BRIEF DESCRIPTION OF THE FIGURES

FIG. 1 demonstrates that the enzyme elastase is able to generate fragments of recombinant RNase L protein, the size of which approximates the fragment of native RNase L protein found in peripheral blood mononuclear cells from patients with MS and CFS.

FIGS. 2 and 3 demonstrate that treatment of a human monocytic cell line, U937, with cefoperazone is able to inhibit the production of the low molecular weight fragment of native RNase L protein, and that the inhibition is dose-dependent.

FIG. 4 demonstrates that cytoplasmic protein extracts from U937 cells previously treated with increasing concentrations of cefoperazone are inhibited from causing the fragmentation of recombinant RNase L protein and that the inhibition occurs in a dose-dependent fashion.

DESCRIPTION OF THE SPECIFIC EMBODIMENTS

Methods for treating a host suffering from a chronic immune disease, e.g., MS or CFS, are provided. In practicing the subject methods, an effective amount of a protease-inhibitory agent, and in many embodiments an elastase-inhibitory agent, e.g., a β-lactam containing agent, is administered to the host. Also provided are compositions and kits thereof for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components that are described in the publications which might be used in connection with the presently described invention.

Treatment Methods

As summarized above, the subject invention provides methods for treating a host suffering from a chronic immune disease. Specifically, the subject invention provides methods of treating a host suffering from MS or CFS, as well as other chronic immune diseases.

In practicing the subject methods, an effective amount of a protease inhibitor, more specifically a serine protease inhibitor, is administered to the patient in need thereof, i.e., the patient suffering from the chronic immune disease. More specifically, an effective amount of an elastase inhibitor is administered to the patient in need thereof. By "inhibit" is meant that these agent at least reduces, if not substantially or complete stops, the protease, e.g., elastase, mediated cleavage of RNase L protein. RNase L protein cleavage-inhibitory agents of interest typically reduce the cleavage or RNase L by at least about 2 fold, usually at least about 3 fold and more usually at least about 5 fold. Any suitable protease, e.g., elastase, inhibitor may be employed.

Of particular interest in certain embodiments are β-lactam containing agents including, but not limited to: penicillins, nocardins, ampicillin, cloxacillin, oxacillin, and piperacillin, cephalosporins and other cephems including, e.g., cefaclor, cefamandole, cefazolin, cefoperazone, cefotaxime, cefoxitin, ceftazidime, ceftriaxone, and cephalothin; and the like. As such, agents of interest include, but are not limited to: Amifloxacin; Amifloxacin Mesylate; Amikacin; Amikacin Sulfate; Aminosalicylic acid; Aminosalicylate sodium; Azlocillin; Aziocillin Sodium; Bacampicillin Hydrochloride; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforamide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chlortetracycline Bisulfate; Chlortetracycline Hydrochloride; Ciprofloxacin; Ciprofloxacin Hydrochloride; Colistin Sulfate; Coumermycin; Coumermycin Sodium; Doxycycline; Doxycycline Calcium; Doxycycline Fosfatex; Doxycycline Hyclate; Droxacin Sodium; Enoxacin; Epicillin; Epitetracycline Hydrochloride; Imipenem; Kanamycin Sulfate; Meclocycline; Minocycline; Minocycline Hydrochloride; Nafcillin Sodium; Norfloxacin; Ofloxacin; Oxytetracycline; Oxytetracycline Calcium; Piperacillin Sodium; Pirbenicillin Sodium; Tetracycline; Tetracycline Hydrochloride; Tetracycline Phosphate Complex; Ticarcillin Cresyl Sodium; Ticarcillin Disodium; Ticarcillin Monosodium; Tobramycin; and Tobramycin Sulfate.

As mentioned above, in the subject methods an effective amount of one or more of the above described active agents is administered to the host, where "effective amount" means a dosage sufficient to produce a desired result, where the desired result is at least an amelioration, if not complete cessation, of the chronic immune disease symptoms. More specifically, the amount of agent that is an effective amount of an agent is an amount that inhibits RNase L protein cleavage, i.e., protects native, high molecular weight RNase L protein from proteolytic attack (e.g., by elastase) and subsequent fragmentation specifically in PBMC. By reducing the amount of RNase L protein fragmentation, the amount of native RNase L protein is increased by at least about 2 fold, usually by at least about 3 fold and more usually by at least about 5 fold, as compared to that observed in a control, e.g., a PBMC from the host that has not been contacted by the active agent(s), when contacted with an effective amount of the inhibitor. While exact amounts may vary depending on the nature of the agent and delivery vehicle employed, and can be readily determined empirically by those of skill in the art, in many embodiments, the amount of agent that is administered in any given dose generally ranges from about 10 micrograms per kilogram total body weight to about 1 gram per kilogram total body weight, usually from about 1 milligram per kilogram total body weight to about 100 milligrams per kilogram total body weight. A particular treatment regimen may include a single dose, or a plurality of different doses administered over various time intervals, e.g., hourly, daily, weekly, monthly, etc.

In the subject methods, the active agent(s) may be administered to the host using any convenient means capable of resulting in the desired treatment. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intratracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

As mentioned above, by treatment is meant that at least an amelioration of the symptoms associated with the chronic immune disease, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the chronic immune disease condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In many embodiments, the hosts or subjects treatable according to the subject methods are those that test positive for the presence of RNase L fragments using the methods described in U.S. Pat. No. 6,080,544 and U.S. patent application Ser. No. 09/645,071; the disclosures of which are herein incorporated by reference.

In certain embodiments, the subject methods comprise diagnosing a subject as having a chronic immune disease as described in U.S. Pat. No. 6,080,544 and U.S. patent application Ser. No. 09/645,071; the disclosures of which are herein incorporated by reference; followed by treating positively diagnosed subjects with an elastase inhibitor according to the present invention, as described above.

Though not binding the invention described in this application to any particular mechanism and solely for purposes of illustration only, one representative mechanism by which the subject methods work is as follows. The data presented herein indicate that the formation of the low molecular weight form of RNase L protein is the result of the action of one or more cellular proteases on the native, high molecular weight RNase L protein. One such protease to be recently identified is the serine protease elastase, as for instance leukocyte or lysosomal elastase, EC # 3.4.21.37, an enzyme contained within the granules of neutrophils. Elastase is known to possess broad proteolytic activity with a large potential for tissue destruction at sites of neutrophil inflammation (Henson, et al. (1987), *J. Clin. Invest.* 79:669-674; Dallegri, et al (1997), *Inflamm. Res.* 46:383-391). In vitro, the results provided herein demonstrate that the addition of elastase to human recombinant RNase L protein results in the production of fragments similar in molecular weight to those found in the PBMCs of patients with CFS and MS (data included herein).

Clearly, then, a compound or compounds that inhibits the action of elastase (i.e., elastase inhibitors) has therapeutic utility in those patients with CFS or MS, particularly in whom is demonstrated the presence of low molecular weight RNase L protein fragments within circulating PBMCs.

A number of research reports have focused on the ability of antibiotics of the class cephalosporin, as well as other antibiotics containing beta-lactam rings, to selectively inhibit serine proteases including elastase in vitro (Balsamo, et al. (2001), *Eur. J. Med. Chem* 36:185-193; Wilmouth, et al. (1998), *Biochemistry* 37:17506-17513; Wilmouth, et al. (1999), *Biochemistry* 38:7989-7998; Buynak, et al. (1997) *J. Med. Chem.* 40:3423-3433; Alpegiani, et al. (1994), *J. Med. Chem.* 37:4003-4019; Knight, et al. (1992), *Biochemistry* 31:4980-4986). More recently, a third generation cephalosporin, cefoperazone, has been demonstrated to reduce the level of inactivation of alpha-1-antitrypsin by activated neutrophils through the direct interaction of the drug with hydrochlorous acid (HOCl) that prevents the HOCl from inactivating alpha-1-antitrypsin (Dallegri, et al., (1999), *Antimicrob.*

Agents. Chemother. 43:2307-2310). Since the presence of alpha-1-antitrypsin is necessary to prevent the activity of elastase, the administration of cefoperazone reduces, either directly or indirectly, the level of elastase activity in patient PBMCs, resulting in a reduction in the elastase-mediated cleavage of RNase L. Subsequently, intact native RNase L, in the presence of 2'5'A trimers and tetramers, etc., would become activated, homodimerize and destroy viral RNA and induce the cell towards programmed cell death (apoptosis) to remove the damaged cell from the system.

Kits

Kits with unit doses of the active agent, usually in oral or injectable doses, are provided. Preferred compounds and unit doses are those described herein above. In such kits, in addition to the containers containing the unit doses will be an informational package insert describing the use and attendant benefits of the drugs in treating pathological condition of interest. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. In Vitro Effects of Elastase on Recombinant RNase L Protein

A. Procedures

1. Digestion of Recombinant RNase L with Elastase

Recombinant RNase L protein (rRNase L) was commercially prepared by in vitro expression in baculovirus of the full-length cDNA encoding the protein sequence for native RNase L (Zhou et al. (1993) *Cell* 72:753-765). The cDNA sequence was inserted into an expression vector that attaches six histidine residues (referred to as a '6His tag') to the amino acid terminal (N-terminal) sequence of the native RNase L protein when the protein is expressed in baculovirus. The resultant 6His-RNase L protein was purified by affinity column chromatography selective for the 6His tag, then eluted with imidazole buffer and subsequently dialyzed versus Tris buffer at pH 8.5. Upon analysis by sodium dodecyl sulfate polyacrylamide gel electrophoresis (SDS-PAGE) and silver staining, the purification resulted in a product of full length, rRNase L that was >95 percent pure.

The purified rRNase L was subjected to proteolytic cleavage, using a commercially available preparation of elastase (Sigma Chemical Company, Cat. No. E 8140). One microgram of rRNase L was treated with 0.001 unit of elastase for 15 minutes at 37 degrees C. The reaction was terminated by adding an excess of bovine serum albumin and placing the mixture on ice. To compare the size of the fragments of rRNase L generated by elastase digestion to the size of the fragments of native RNase L as found in peripheral blood mononuclear cells (PBMCs), an extract of proteins from PBMCs from a patient with CFS was included. The method of isolation, extraction, and analysis of PBMCs is described below.

2. Quantification of 2-5A Binding Proteins

Analysis of all RNase L protein species and fragments that retained the 2-5A-binding site—whether from recombinant sources (e.g., baculovirus) or native sources (e.g., peripheral blood mononuclear cells)—was performed using a radio labeled 2-5A trimer and SDS-PAGE as described by the method of Charachon et al. (1990), *Biochemistry* 29:2550-2556. Briefly, 2-5A trimer was radio labeled by the ligation of $^{32}$P-pCp to the 3' end (method of Charachon). After removal of the 3' terminal phosphate by treatment with bacterial alkaline phosphatase, the 3' ribose residue of pC was oxidized with sodium metaperiodate (10 mM final concentration, pH 4.75) for one hour at 4 C to form 2-5A-$^{32}$P—C—OX. This reaction mixture was subsequently equilibrated to pH 8.0 by the addition of NaOH. This oxidized molecule was used as the radiolabel in all subsequent reactions for RNase L protein analysis (referred to below as radio labeled 2-5A).

To demonstrate the binding of 2-5A by rRNase L protein and fragments thereof, the radio labeled 2-5A was incubated with 0.1 microgram of elastase-digested recombinant RNase L protein at 2-4 C. for 15 minutes to allow the radio labeled 2-5A to interact with any 2-5A-binding proteins present, such as the full length rRNase L protein and all lower molecular weight species still retaining the 2-5A binding site. The 2-5A radiolabel was then covalently attached to the rRNase L protein and all lower molecularweight species present still retaining the binding site bythe addition of cyanoborohydride (20 mM in 100 mM phosphate buffer, pH 8.0). The reduction reaction was allowed to occur for 20 minutes at room temperature. SDS-PAGE sample buffer, including a tracking dye, was added to the samples and all samples were incubated at 95 C. for 5 minutes under reducing conditions.

The samples were then subjected to standard SDS-polyacrylamide gel electrophoresis using a 4 percent stacking gel and a 10 percent separating gel (Bisbal et al.(1989), *European Journal of Biochemistry* 179:595-602). Also included in the first lane of each gel was a molecular weight marker, prestained to be visible as it migrated during the course of electrophoresis (Bio-Rad Laboratories). The gel was electrophoresed until the tracking dye had migrated to the bottom of the gel (approximately 5 hours at a constant current of 30 mAmps). The gel was then dried and subjected to autoradiography (Bio-Rad Laboratories FX Imager).

The autoradiographs were then analyzed by densitometry, and quantification of any and all RNase L protein species present was performed using specialized software (Quantity One from Bio-Rad Laboratories).

B. Results

In FIG. 1, Lane #1 contains the molecular weight markers. (Lane #1—Molecular weight markers. Arrows to left of figure indicate listed molecular weights in kDa. Arrows to right of figure indicate full length rRNase L protein at approximately 80 kDa, and 37 kDa RNase L protein fragment.) In Lane #2, a protein extract of PBMCs from a patient with CFS demonstrates the presence of the low molecular weight (LMW) 2-5A-binding RNase L protein at 37 kDa (indicated by an arrow) and the native RNase L protein at 83 kDa (indicated by an arrow)(rRNase L protein incubated with PBMC cytoplasmic protein extract from patient with CFS.). In Lane #3, digestion of rRNase L with elastase demonstrates the presence of a low molecular weight 2-5A-binding protein equivalent in size with the LMW RNase L protein fragment in Lane #2(rRNase L protein incubated with elastase in buffer.). In Lane #4, the undigested rRNase L protein is demonstrated to be equivalent in size to the native RNase L in the PBMC protein extract in Lane #2(rRNase L protein incubated with buffer only.).

C. Discussion

From FIG. 1, treatment of rRNase L protein results in fragmentation of rRNase L protein into a protein with the equivalent low molecular weight size (i.e., 37 kDa) as detected in protein extracts from PBMCs from patients with CFS.

II. In Vitro Effects of Cefoperazone on the Levels of RNase L Protein in the Human Monocytic Leukemia Cell Line U937

A. Procedures

1. In Vitro Culture, Propagation, and Treatment of U937 Cells with Cefoperazone

The human monocytic cell line, U937 (Sundstrom, et al. (1976) *Int. J. Cancer* 17:565-577) was obtained from the American Type Culture Collection (ATCC Cat. No. CRL-1593) and cultured under condition as suggested by the ATCC. The standard growth medium employed was RPMI 1640 (Life Technologies), supplemented with ten percent (10%) fetal bovine serum (FBS; Life Technologies). This medium, RPMI 1640+10% FBS, was used for all subsequent culture and experiments.

Since U937 cells are grown in suspension, cultures were grown to a density of approximately 2 million cells per mL (referred to herein as 'confluent'). Confluent cultures of U937 cells were treated with various concentrations of cefoperazone under various conditions.

In the first condition (Regimen #1), confluent cultures of U937 cells were allowed to remain in culture for an additional 7 days without feeding or media supplementation in order to induce the cells to begin to undergo apoptosis, resulting in the fragmentation of native RNase L (among other proteins). After 7 days of confluency, the U937 cells were then treated for an additional 72 hours under standard cell culture conditions with or without various concentrations of cefoperazone. Typically, 5-10 mLs of confluent U937 cells were used per concentration of drug.

After incubation with or without drug, the U937 cells were removed from cell culture and centrifuged at 500×g for 5 minutes. The supernatant was discarded and the resultant U937 cell pellet was washed once with 10 mLs of PBS and centrifuged for 5 minutes at 500×g. The supernatant was the discarded and the resultant pellet was resuspended in 1 mL of PBS, placed into a microcentrifuge tube, and centrifuged at highest speed for one minute in a microcentrifuge. The supernatant was discarded and the resultant cell pellet was then stored at −70° C. until the protein extraction procedure could be performed.

In another treatment regimen (Regimen #2), specific concentrations of cefoperazone were added to U937 cells at confluency (i.e., at the day at which the cultures reached maximum density, Day 0), or at Day 5 after reaching confluency, or at Day 12 after reaching confluency. In all cases the cells then remained in culture without supplementation of media for an additional 3 days and were then harvested exactly as described above.

2. Protein Extraction and Quantification

To extract the proteins from the U937 cell pellet, the pellet was resuspended in a volume approximately 5-10 times the packed cell volume in the extract buffer (10 mM HEPES, pH 7.6, 90 mM KCl, 1.5 mM $Mg(OAc)_2$, 0.5% non-ionic detergent (such as Nonidet P-40 or Igepal CA-630, Sigma Chemical Corporation)). The extract buffer also contained a mixture of protease inhibitors to help stabilize the extract and impeded the action of proteases. One such commercially available mixture is the MiniComplete protease inhibitor cocktail (Boehringer-Mannheim) containing aprotinin, leupeptin, pefabloc-SC and EDTA.

The extraction procedure was performed at 2-4 degrees C., holding the cell pellet-extraction buffer in ice water or on wet ice for 5 minutes. The cell pellet-buffer mix was then vortexed at medium speed for 2 minutes at room temperature to ensure complete solubilization of the cell membranes. The cell pellet-buffer mix was then placed at 2-4 C. for an additional 5 minutes. The final step was to centrifuge the cell pellet-buffer mix at high speed in a microcentrifuge (16,000×g) for 2 minutes. The supernatant containing the proteins of interest (referred to as 'cell cytoplasmic protein extracts') was collected and the cell pellet was discarded. All cell cytoplasmic protein extracts were stored at −70 C. until further analysis could be performed.

Quantification of proteins in the cell cytoplasmic protein extracts was performed using a standard commercially available procedure of a modified Bradford method (Bio-Rad Laboratories) following the manufacturer's recommended procedure.

3. Analysis of 2-5A Binding Proteins in U937 Cell Cytoplasmic Protein Extracts

The analysis and quantification of 2-5A binding proteins in the U937 cell cytoplasmic protein extracts was performed exactly as outlined above according to the method of Charachon, et al. (see above), with the following modification: The radio labeled 2-5A was incubated with 200 micrograms of U937 cell cytoplasmic protein extract at 2-4 C. for 15 minutes to allow the radio labeled 2-5A to interact with any 2-5A-binding proteins present, such as the full length native RNase L protein and all lower molecular weight species still retaining the 2-5A binding site. The remainder of the procedure and subsequent analysis by SDS-PAGE and densitometry were performed as described above. The results are expressed as the density (or relative amount) of the 37 kDa lower molecular weight fragment of RNase L protein present divided by the density (or relative amount) of full length RNase L protein present, multiplied by a constant factor of 10.

B. Results

In FIG. 2, the results of treatment Regimen #1 are displayed. Lane #1 contains the molecular weight markers (Molecular weight markers. Arrows to left of figure indicate listed molecular weights in kDa. Arrows to right of figure indicate full length RNase L protein at approximately 80 kDa (upper arrow) and 37 kDa RNase L protein fragment (lower arrow)). Lane #2 represents U937 cells after 7 days of confluency and before treatment (PBMC cytoplasmic protein extract from patient with CFS, demonstrating the presence of native and fragmented RNase L protein). (Lane #3 represents U937 cells after 1 day of confluency, to indicate the increase in fragmentation of RNase L over time in culture)(U937 cytoplasmic protein extract from cells prepared 7 days after confluency.). In Lanes #4-10, increasing amounts of cefoperazone are added to the culture medium for 72 hours before analysis of 2-5A-binding proteins (U937 cytoplasmic protein extract from cells prepared 7 days after confluency and treated for an additional 3 days with the following concentrations of cefoperazone: None (Lane #4); 10 micrograms/mL (Lane #5); 50 micrograms/mL (Lane #6); 100 micrograms/mL (Lane #7); 500 micrograms/mL (Lane #8); 1000 micrograms/mL (Lane #9); and 5000 micrograms/mL (Lane #10).). The ratio of LMW to HMW RNase L protein (multiplied by a constant factor of 10) is listed for each lane (The ratios are listed below each lane as the relative amount of 37 kDa RNase L protein divided by the relative amount of native RNase L protein, multiplied by a constant factor of 10.).

In FIG. 3, the results of treatment Regimen #2 are displayed. Lane #1 contains the molecular weight markers (Molecularweight markers. Arrows to left of figure indicate listed molecular weights in kDa. Arrows to right of figure indicate full length RNase L protein at approximately 80 kDa (upper arrow) and 37 kDa RNase L protein fragment (lower arrow).). Lanes #2-4 represent U937 cells at confluency (Day 0) treated for 3 days with cefoperazome (the concentrations shown above each lane are in micrograms/mL) (Freshly cultured U937 cells treated for 3 days with the following concentrations of cefoperazone: Lane #2, none; Lane #3, 100 micrograms/mL; Lane #4, 500 micrograms/mL.). Lanes #5-7 represent U937 cells treated with cefoperazone starting at confluency plus five days (Day 5)(U937 cells cultured for 5 days, then treated for 3 days with the following concentrations of cefoperazone: Lane #5, none; Lane #6, 100 micrograms/mL; Lane #7, 500 micrograms/mL.). Lanes 8-10 represent U937 cells treated with cefoperazone starting at confluency plus twelve days (Day 12)(U937 cells cultured for 12 days, then treated for 3 days with the following concentrations of cefoperazone: Lane #8, none; Lane #9, 100 micrograms/mL; Lane #10, 500 micrograms/mL.). The corresponding ratio of LMW RNase L protein (37 kDa) to HMW RNase L protein is listed at the bottom of each lane (The ratios are listed below each lane as the relative amount of 37 kDa RNase L protein divided by the relative amount of native RNase L protein, multiplied by a constant factor of 10.).

C. Discussion

From FIG. 2, increasing amounts of cefoperazone reduce the level of RNase L fragmentation in vitro as demonstrated by a reduction in the ratio of LMW to HMW RNase L protein observed. Significant decrease occurs at a concentration of 100 micrograms of cefoperazone per mL of culture medium.

From FIG. 3, increasing amounts of cefoperazone reduce the level of RNase L fragmentation in vitro as demonstrated by a reduction in the ratio of LMW to HMW RNase L protein observed. At Days 5 and 12, a significant decrease in the ratio occurs at a concentration of 100 micrograms of cefoperazone per mL of culture medium. At Days 0, 5, and 12, a significant decrease in the ratio occurs at a concentration of 500 micrograms of cefoperazone per mL of culture.

III. In Vitro Effects of Cefoperazone-Treated U937 Cell Cytoplasmic Protein Extracts on the Levels of Elastase Activity A. Procedures 1. Incubation of U937 Cell Cytoplasmic Protein extracts and rRNase L protein U937 cell cytoplasmic protein extracts produced after treatment of U937 cells with cefoperazone in treatment Regimen #1 (see above) were quantified for protein content (see above), then mixed with rRNase L protein that had been previously radio labeled with 2-5A according to the protocol as described above. Briefly, 15 micrograms of U937 cell cytoplasmic protein extract was mixed with 0.1 microgram of $^{32}$P-2-5A-radio labeled rRNase L for a fixed incubation period (5 minutes) at 37 C. The reaction was terminated by the addition of 2×SDS-PAGE loading buffer, the samples were prepared and electrophoresed as described above and analyzed using densitometry.

B. Results

In FIG. 4, Lane #1 indicates the molecular weight markers (Molecular weight markers. Arrows to left of figure indicate listed molecular weights in kDa. Arrows to right of figure indicate full length rRNase L protein at approximately 80 kDa (upper arrow) and 37 kDa RNase L protein fragment (lower arrow).). In Lanes #2-7, DSD-PAGE demonstrated the amount of fragmentation that occurs after cytoplasmic protein extracts from U937 cells (previously treated in vitro with increasing concentrations of cefoperazone for 72 hours) were reacted with $^{32}$P-2-5A-radio labeled rRNase L.

Lane #2—rRNase L protein incubated with PBMC cytoplasmic protein extract from patient with CFS.

Lane #3—rRNase L protein incubated with elastase in buffer.

Lane #4—rRNase L protein incubated with buffer only.

Lane #5—rRNase L protein incubated with cytoplasmic protein extract from U937 cells prepared 7 days after confluency.

Lanes #6 through #11—rRNase L protein incubated with cytoplasmic protein extract from U937 cells prepared 7 days after confluency and treated for an additional 3 days with the following concentrations of cefoperazone: None (Lane #6); 10 micrograms/mL (Lane #7); 50 micrograms/mL (Lane #8); 100 micrograms/mL (Lane #9); 500 micrograms/mL (Lane #10); and 1000 micrograms/mL (Lane #11).

The corresponding ratio of LMW rRNase L protein (37 kDa) to HMW rRNase L protein is listed at the bottom of each lane.

C. Discussion

In FIG. 4, cytoplasmic protein extracts from U937 cells previously treated in vitro with cefoperazone demonstrate a marked inhibition of elastase activity as indicated by a reduction in the amount of LMW rRNase L protein generated after incubation of cytoplasmic extract and pre-labeled HMW rRNase L.

It is evident from the above results and discussion that relatively simple and rapid methods are provided for diagnosing and/or characterizing chronic immune disease (e.g. MS or CFS) activity in a subject are provided. With the subject methods, accurate diagnosis of the chronic immune disease condition, as well the identification of the stage and/or progression of the chronic immune disease condition, may be obtained. As such, the subject methods provide for more accurate diagnostic and/or treatment regimens. In addition, methods of treating hosts for chronic immune disease are provided. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail byway of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for treating a host suffering from a chronic immune disease, said method comprising:
   (a) administering to said host an effective amount of a β-lactam containing compound to treat said host for said chronic immune disease.

2. The method according to claim 1, wherein said chronic immune disease is selected from the group consisting of CFS and MS.

3. The method according to claim 1, wherein said β-lactam containing compound is a cephem.

4. The method according to claim 3, wherein said cephem compound is cefoperazone.

5. The method according to claim 1, wherein said host is a mammal.

6. The method according to claim 5, wherein said mammal is a human.

7. The method according to claim 1, wherein said host is diagnosed as having said chronic immune disease prior to said administering step.

8. The method according to claim 7, wherein said host is diagnosed by detecting the presence of RNase L fragments.

9. A method for treating a host suffering from chronic fatigue syndrome, said method comprising:
   (a) administering to said host an effective amount of a protease inhibitor to treat said host for said chronic fatigue syndrome.

* * * * *

UNITED STATES PATENT AND TRADEMARK OFFICE
CERTIFICATE OF CORRECTION

| | | |
|---|---|---|
| PATENT NO. | : 7,754,707 B2 | |
| APPLICATION NO. | : 10/882993 | |
| DATED | : July 13, 2010 | |
| INVENTOR(S) | : El Bakkouri et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1770 days.

Signed and Sealed this
Tenth Day of May, 2011

David J. Kappos
*Director of the United States Patent and Trademark Office*